United States Patent
Fujii

(10) Patent No.: US 9,671,606 B2
(45) Date of Patent: Jun. 6, 2017

(54) ILLUMINATION OPTICAL SYSTEM FOR ENDOSCOPE

(71) Applicant: HOYA CORPORATION, Tokyo (JP)

(72) Inventor: Hiroaki Fujii, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/911,578

(22) PCT Filed: Aug. 5, 2014

(86) PCT No.: PCT/JP2014/004092
§ 371 (c)(1),
(2) Date: Feb. 11, 2016

(87) PCT Pub. No.: WO2015/022774
PCT Pub. Date: Feb. 19, 2015

(65) Prior Publication Data
US 2016/0195706 A1  Jul. 7, 2016

(30) Foreign Application Priority Data
Aug. 13, 2013 (JP) .................................. 2013-167998

(51) Int. Cl.
*A61B 1/06* (2006.01)
*A61B 1/07* (2006.01)
(Continued)

(52) U.S. Cl.
CPC ...... *G02B 23/2469* (2013.01); *A61B 1/00096* (2013.01); *A61B 1/00137* (2013.01);
(Continued)

(58) Field of Classification Search
CPC ............ A61B 1/00096; A61B 1/00165; A61B 1/00167; A61B 1/07; A61B 1/06; G02B 23/2469; G02B 6/005
See application file for complete search history.

(56) References Cited

U.S. PATENT DOCUMENTS 4,017,150 A * 4/1977 Imai ................... A61B 1/00096
385/119
4,272,156 A 6/1981 Ishibashi et al.
(Continued)

FOREIGN PATENT DOCUMENTS

JP  54-89749  7/1979
JP  61-244322  10/1986
(Continued)

OTHER PUBLICATIONS

Search Report for PCT/JP2014/004092, mailing date of Nov. 11, 2014.
(Continued)

*Primary Examiner* — John P Leubecker
(74) *Attorney, Agent, or Firm* — Greenblum & Bernstein, P.L.C.

(57) ABSTRACT

An illumination optical system for an endoscope includes two light guides disposed in an insertion tube in a first direction to sandwich a center of the insertion tube therebetween; an observation window on a tip end face of the insertion tube; two concave lens parts having negative powers sandwiching the observation window at positions facing end faces of two light guides on the tip end face of the insertion tube. The end face of each of the two light guides has a smaller width in the first direction than a width in a second direction perpendicular to the first direction; each of the two concave lens parts has a larger negative power in the first direction than a negative power thereof in the second direction; and of illumination light which has propagated through each of the two concave lens parts after being emitted from each of the two light guides.

3 Claims, 7 Drawing Sheets

(51) Int. Cl.
*G02B 23/24* (2006.01)
*G02B 23/26* (2006.01)
*A61B 1/00* (2006.01)
*A61B 1/05* (2006.01)
*F21V 8/00* (2006.01)

(52) U.S. Cl.
CPC ............ *A61B 1/00163* (2013.01); *A61B 1/05* (2013.01); *A61B 1/0661* (2013.01); *A61B 1/07* (2013.01); *G02B 6/0008* (2013.01); *G02B 23/24* (2013.01); *G02B 23/26* (2013.01); *G02B 6/005* (2013.01)

(56) References Cited

U.S. PATENT DOCUMENTS

| | | | |
|---|---|---|---|
| 4,529,267 A * | 7/1985 | Nishioka | A61B 1/00096 385/117 |
| 5,577,992 A | 11/1996 | Chiba et al. | |
| 8,118,734 B2 | 2/2012 | Murayama | |
| 2001/0003142 A1 * | 6/2001 | Koshikawa | A61B 1/00096 600/177 |
| 2008/0242935 A1 | 10/2008 | Inoue | |
| 2013/0267857 A1 | 10/2013 | Takimura | |

FOREIGN PATENT DOCUMENTS

| | | |
|---|---|---|
| JP | 61-344322 | 10/1986 |
| JP | 7-204158 | 8/1995 |
| JP | 7-204159 | 8/1995 |
| JP | H09-68659 | 3/1997 |
| JP | 11-326786 | 11/1999 |
| JP | 2003-235787 | 8/2003 |
| JP | 2009-22374 | 2/2009 |
| JP | 2009-23374 | 2/2009 |
| JP | 2009-207529 | 9/2009 |
| JP | 2010-119430 | 6/2010 |
| JP | 4704386 | 6/2011 |
| JP | 2014-54369 | 3/2014 |
| WO | 2012/081599 | 6/2012 |

OTHER PUBLICATIONS

International Preliminary Report on Patentability issued in PCT/JP2014/004092 mailed Feb. 16, 2016.
International Preliminary Report on Patentability issued in PCT/JP2014/004092 mailed Feb. 25, 2016.
Office Action issued in China Counterpart Patent Appl. No. 201480045178.6, dated Oct. 27, 2016, along with an English translation thereof.
Office Action issued in European Patent Office (EPO) Counterpart Patent Appl. No. 14836238.7, dated Apr. 13, 2017.

* cited by examiner

[Fig. 1]
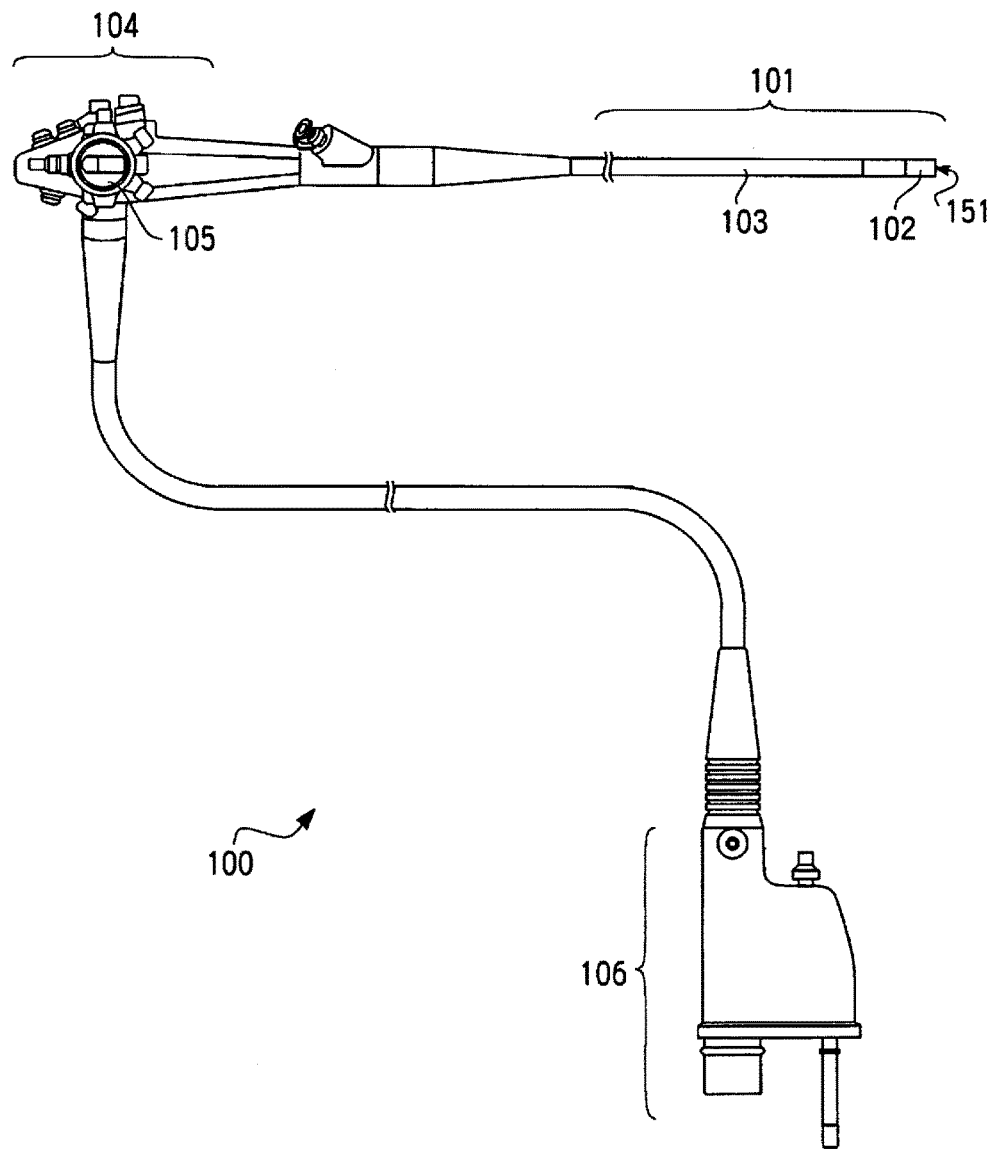

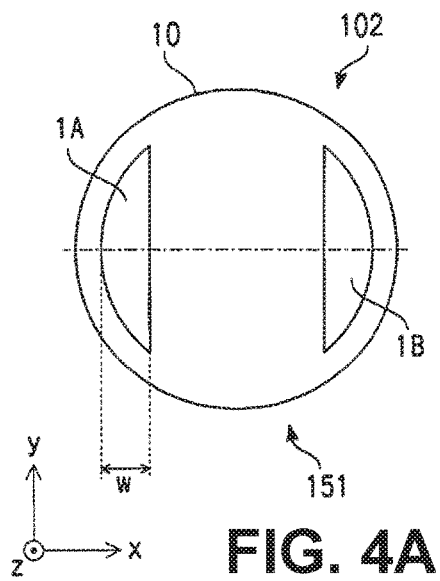
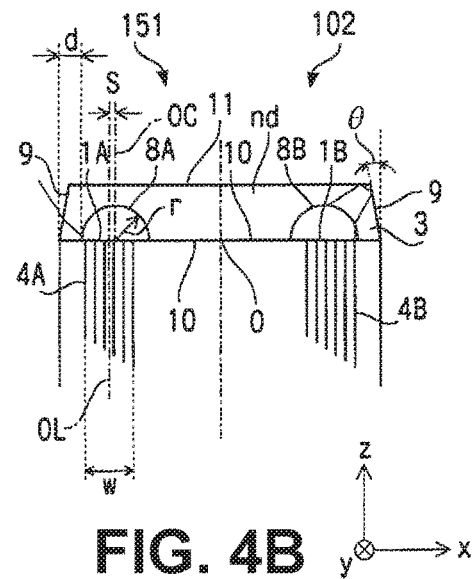
FIG. 4A    FIG. 4B
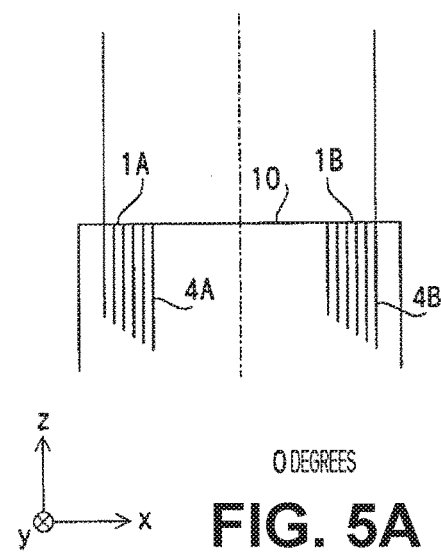
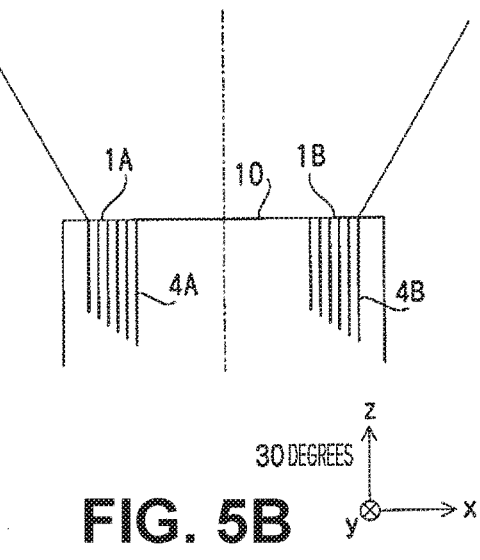
FIG. 5A    FIG. 5B

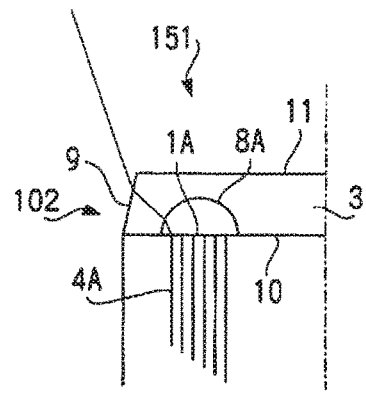
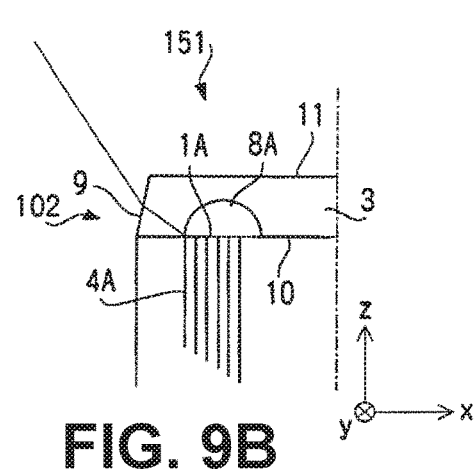
FIG. 9A  FIG. 9B
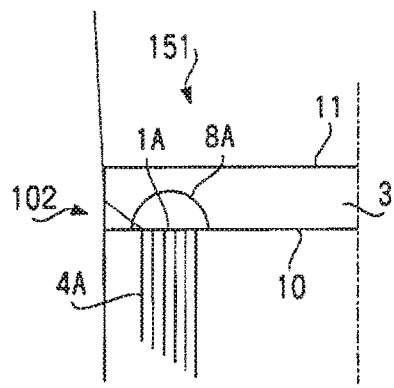
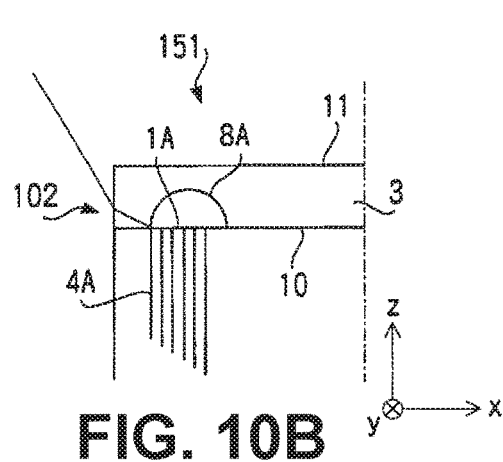
FIG. 10A  FIG. 10B
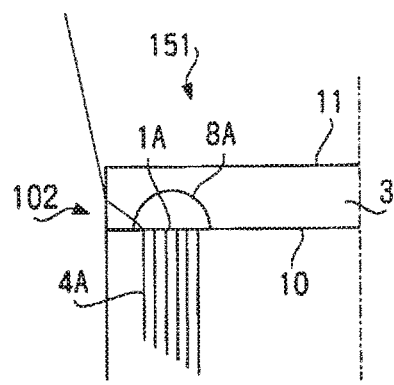
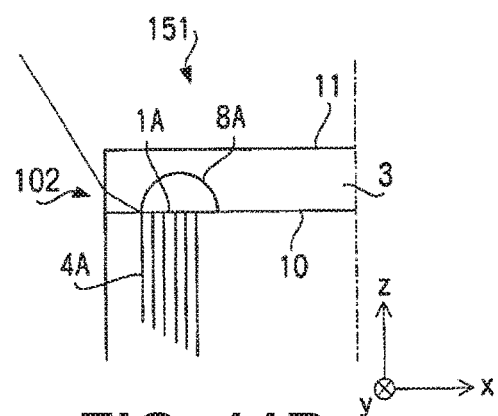
FIG. 11A  FIG. 11B

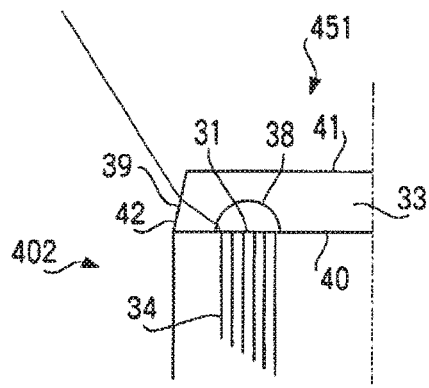
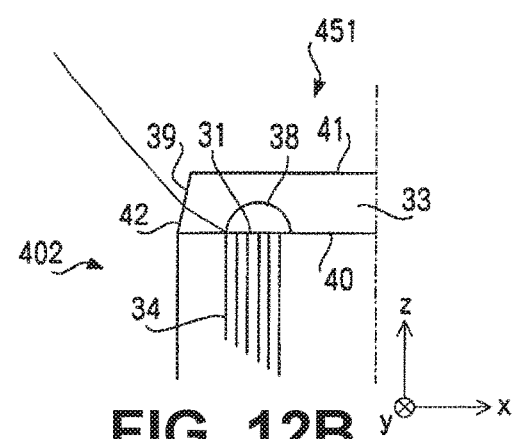
FIG. 12A  FIG. 12B
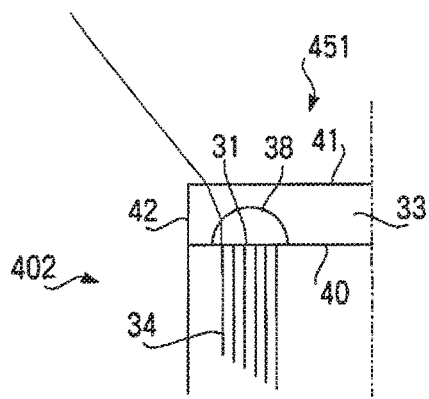
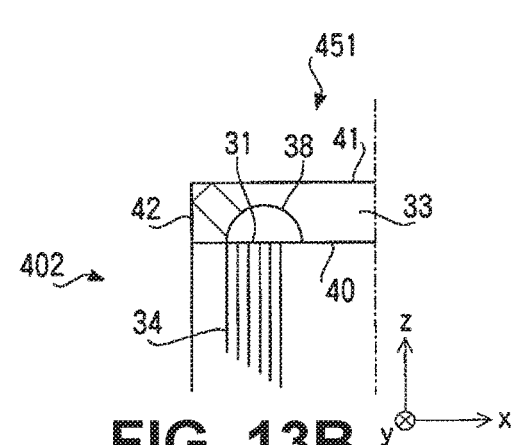
FIG. 13A  FIG. 13B
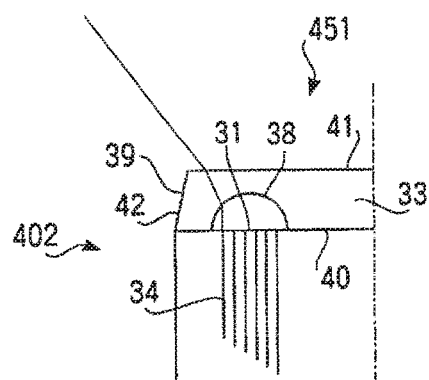
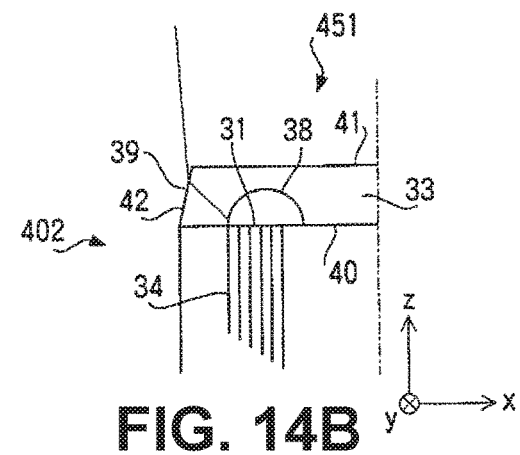
FIG. 14A  FIG. 14B

[Fig. 15]
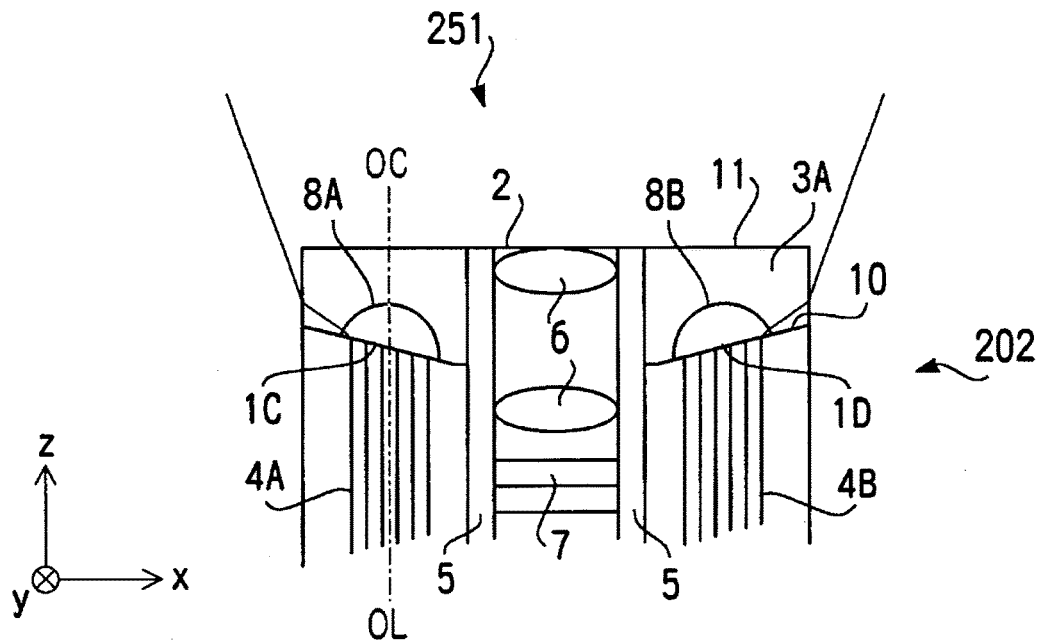
[Fig. 16]
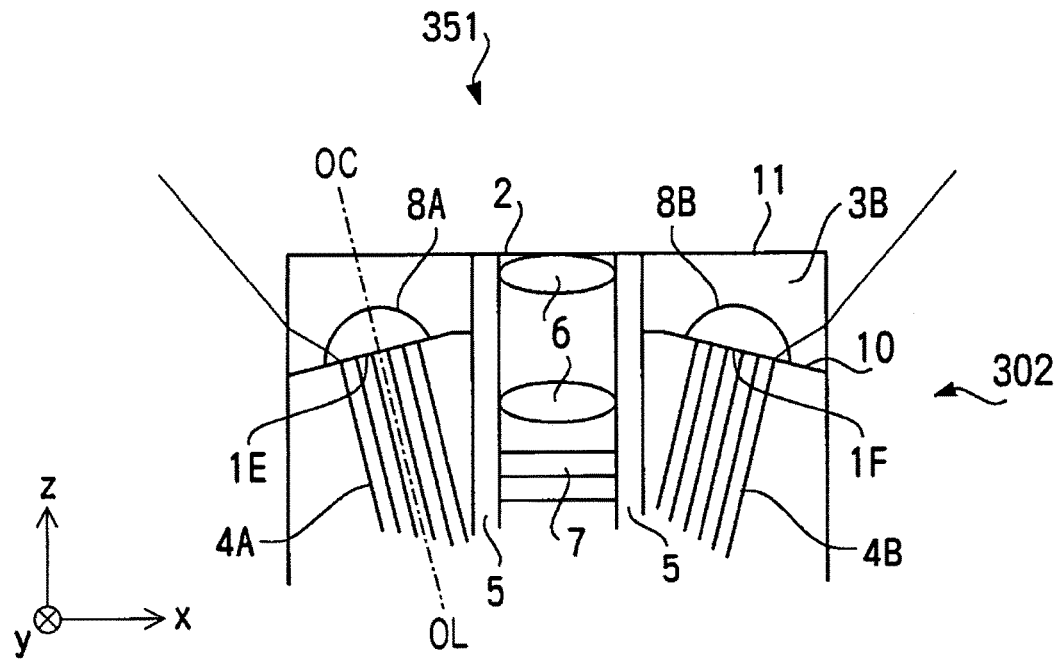

ILLUMINATION OPTICAL SYSTEM FOR ENDOSCOPE

TECHNICAL FIELD

The present invention relates to an illumination optical system used for an endoscope.

BACKGROUND ART

An endoscope configured such that a light-distribution window through which illumination light for illuminating an observation target area is emitted and an observation window through which the illumination light reflected from the observation target area is received are provided at a tip portion of an insertion tube of the endoscope is known. The insertion tube of the endoscope of this type is formed in a shape of an elastic tube, and a light guide for introducing the illumination light to the tip portion is provided in the inside of the insertion tube. In the observation window, an objective lens is provided, and object light reflected from the observation target area is received by an image pickup device, such as a CCD (Charge Coupled Device), via the objective lens. The object light received by the image pickup device is subjected to signal processing and is displayed as a picked up image on a monitor. As a result, an operator of the endoscope becomes able to operate the endoscope while observing the image displayed on the monitor.

In general, as a monitor on which an image is displayed, a monitor having a laterally long aspect ratio, such as 4:3 or 16:9, is used. Therefore, if an aspect ratio of an emitted light distribution of illumination light emitted from the light guide does not coincide with the aspect ratio of the monitor, it becomes impossible to use the whole monitor screen effectively or the brightness of the image decreases because an area not displayed on the monitor is illuminated.

Japanese Patent Provisional Publication No, 2009-207529A (hereafter, referred to as patent document 1) describes an endoscope capable of obtaining a bright image. The endoscope described in patent document 1 includes a ring-shaped light guide in an insertion tube of the endoscope and is provided with a transparent cap at a tip portion of the insertion tube. The illumination light emitted from the light guide propagates through the inside of the cap, and is emitted from the tip portion. Around the periphery of the cap, an inclined surface is formed, and the inclined surface functions as a convex lens. Therefore, the illumination light which has propagated through the inside of the cap and passed through the inclined surface is emitted from the tip portion in a converged state. As a result, it becomes possible to prevent the illumination light from being scattered.

Japanese Patent Publication No. 4704386 (hereafter, referred to as patent document 2) describes an endoscope which includes a light guide having an exit end face of which cross sectional shape has different lengths between a left and right direction and a longitudinal direction (i.e., an elliptical shape). At a tip portion of an insertion tube of the endoscope of patent document 2, a transparent cap is provided. At a position of the transparent cap corresponding to the exit end face of the light guide, a light scattering part which is formed in a recessed shape to scatter transmitted illumination light is provided. The light scattering part has different lengths between a left and right direction and a longitudinal direction in conformity with the cross sectional shape of the exit end face of the light guide, and has the negative refractive power which varies depending on the length. Therefore, it is possible to change the degree of scattering of the illumination light between the left and right direction and the longitudinal direction, and thereby it becomes possible to bring the intensity distribution of the illumination light close to the aspect ratio of the monitor.

SUMMARY OF INVENTION

Since in the endoscope described in patent document 1, a ring-shaped fiber is used as the light guide, the intensity distribution of the emitted illumination light becomes a circular shape or a ring shape having a ratio of 1:1 between the left and right direction and the longitudinal direction. Therefore, when a monitor having a laterally long aspect ratio is used, the amount of illumination light at the left and right ends on the screen becomes small or areas outside the screen in the longitudinal direction may be illuminated uselessly. In this case, the illumination light cannot be used effectively. Further, since the ring-shaped fiber is used, the diameter of the tip portion of the insertion tube is determined depending on the shape of the fiber, and therefore it is difficult to decrease the diameter of the tip portion.

Since the endoscope described in patent document 2 is provided with, at the tip portion of the insertion tube, the light scattering part having power which is different between the longitudinal direction and the left and right direction, it is possible to bring the intensity distribution of the emitted illumination light close to the aspect ratio of the monitor. However, there is a problem that, for the light guides disposed on the left and right sides with respect to the center of the insertion tube, the refractive power of the light scattering part in the longitudinal direction is extremely small relative to the refractive power in the left and right direction and therefore almost no scattering effect is obtained in the longitudinal direction because the light scattering part is formed in a ring shape which is coaxial with the center of the tip portion. The scattering effect of the light scattering part is determined by the curvature of a surface of a lens shape and the refractive index of the light scattering part, and therefore there is a case where the adequate light scattering effect cannot be achieved. Further, there is a case where the illumination light which has been scattered by the light scattering part and has propagated through the inside of the cap is reflected by an exit end face of the cap, and the scattering effect and the amount of emitted light is decreased.

The present invention is made in view of the above described circumstances. That is, the object of the present invention is to provide an illumination optical system for an endoscope configured such that a diameter of an insertion tube is made small, the scattering effect of illumination light is enhanced, and thereby the intensity distribution of emitted illumination light is made consistent with the aspect ratio of a monitor and an observation area defined through an observation window.

To achieve the above described object, according to an aspect of the invention, there is provided an illumination optical system for an endoscope provided in an elastic insertion tube of an endoscope, comprising: two light guides disposed in the insertion tube to be arranged in a first direction to sandwich a center of the insertion tube therebetween; an observation window disposed on a tip end face of a tip portion of the insertion tube; two concave lens parts having negative powers, the two concave lens parts being disposed to sandwich the observation window at positions facing end faces of the two light guides on the tip end face of the insertion tube. In this configuration, on the tip end face of the tip portion of the insertion tube, the end face of each of the two light guides has a smaller width in the first direction than a width thereof in a second direction perpendicular to the first direction. Each of the two concave lens parts has a larger negative power in the first direction than a negative power thereof in the second direction. Of illumination light which has propagated through each of the two concave lens parts after being emitted from each of the two light guides, an optical path of light which has propagated through a center of each of the two light guides and has been emitted from a center of each end face of each of the two light guides is inclined outward in the first direction with respect to an axis direction of the insertion tube.

With this configuration, the illumination light emitted from the light guides are scattered by the concave lens parts. Since the scattering effect in the first direction is larger than that in the second direction and the exit direction of the illumination light is inclined toward the first direction, the intensity distribution of the emitted illumination light spreads in the first direction. As a result, a wide area can be illuminated with the illumination light, and the wide area can be observed through the observation window. Since the intensity distribution of the illumination light spreads in the direst direction, it becomes possible to bring the aspect ratio of the illumination light be consistent with the aspect ratio is a monitor having a laterally long aspect ratio when an image of the area observed through the observation window is displayed on the monitor. Consequently, the illumination light can be used effectively. That is, according to the above described configuration of the illumination optical system, the diameter of the insertion tube is made small, the scattering effect of illumination light is enhanced, and thereby the intensity distribution of emitted illumination light is made consistent with the aspect ratio of a monitor and the observation area defined through the observation window.

The illumination optical system for an endoscope may further comprise a cap having a circular outer shape and made of transparent material for letting the illumination light pass therethrough, and the cap is provided on a front of the end faces of the two light guides. In this case, each of the two concave parts is formed by forming a recessed part on a surface of the cap facing the end faces of the two light guides.

With this configuration, the concave lens part can be formed by a simple structure and at a low cost.

Optical axes of the two concave lens parts may be decentered from optical axes of the two light guides, respectively.

With this configuration, the exit angle of the illumination light emitted from the light guides can be increased by the concave lens part, and by decentering the concave lens part with respect to the light guide, the exit direction of the illumination light can be changed. Therefore, the intensity distribution of the emitted illumination light can be adjusted by the concave lens part and the decentering, and thereby it becomes possible to more easily make the aspect ratio of the intensity distribution of the illumination light be consistent with the aspect ratio of the used monitor.

When w (unit: mm) represents a width of each of the end faces of the two light guides in the first direction, r (unit: mm) represents a curvature radius of each of the two concave lens parts in the first direction, s (unit: mm) represents a decentering amount of the optical axis of each of the two concave lens parts toward a center of the insertion tube with respect to the optical axis of corresponding one of the two light guides, and $n_d$ represents a refractive index at d-line of material of the cap, the illumination optical system may satisfy a condition:

$$2 \times 10^{-3} < (n_d \times w \times s^2)/r < 13 \times 10^{-3}.$$

With this configuration, it becomes possible to increase the scattering effect by the concave lens part, and to decrease the ratio of illumination light which is totally reflected from a boundary of the cap and is confined in the cap. As a result, the amount of emitted light can be increased.

When w (unit: mm) represents a width of each of the end faces of the two light guides in the first direction, d (unit: mm) represents a distance, in the first direction passing through a center of the tip end face of the insertion tube, between an outer edge of the cap and a point on an edge of one of the two concave lens parts nearest to the outer edge of the cap, r (unit: mm) represents a curvature radius of each of the two concave lens parts in the first direction, s (unit: mm) represents a decentering amount of the optical axis of each of the two concave lens parts toward a center of the insertion tube with respect to the optical axis of corresponding one of the two light guides, and n d represents a refractive index at d-line of material of the cap, the illumination optical system may satisfy a condition:

$$15 \times 10^{-6} < (n_d \times w \times d \times s^3)/r < 200 \times 10^{-6}.$$

With this configuration, it becomes possible to increase the scattering effect by the concave lens part, and to decrease the ratio of illumination light which is totally reflected from a boundary of the cap and is confined in the cap. As a result, the amount of emitted light can be increased.

The cap may be formed such that an outer diameter of the cap becomes smaller toward a tip of the insertion tube.

With this configuration, resistance which the insertion tube receives from an inner wall of a body cavity when the insertion tube is inserted into the body cavity can be suppressed, and thereby it becomes possible to easily insert the insertion tube in the body cavity.

On the tip end face of the tip portion of the insertion tube, each of the end faces of the two light guides may be inclined such that each of the end faces of the two light guides becomes lower toward a center of the insertion tube.

With this configuration, since the illumination light is emitted while being refracted outward in the first direction, a laterally long intensity distribution can be achieved as the intensity distribution of the emitted illumination light.

Each of the two light may be disposed in the insertion tube such that, in the tip portion of the insertion tube, each of the two light guides is bent to deviate from a center of the insertion tube toward a tip of the insertion tube. On the tip end face of the tip portion of the insertion tube, the end faces of the two light guides may be inclined to be perpendicular to axis directions of the two light guides, respectively, in such a matter that each of the end faces of the two light guides becomes higher toward the center of the insertion tube.

With this configuration, since the illumination light emitted from the end face of the light guide is emitted outward in the first direction, a laterally long intensity distribution can be achieved as the intensity distribution of the emitted illumination light.

BRIEF DESCRIPTION OF DRAWINGS

FIG. 1 illustrates an outer appearance of an endoscope having an illumination optical system according to an embodiment of the invention.

FIGS. 4A-4B illustrate a tip portion of the insertion tube according to the embodiment of the invention.

FIGS. 5A-5B illustrate cross sections of the tip portion of the insertion tube according to the embodiment of the invention.

FIGS. 9A-9B illustrate cross sections of the tip portion of the insertion tube according to an example 4.

FIGS. 10A-10B illustrate cross sections of the tip portion of the insertion tube according to an example 5.

FIGS. 11A-11B illustrate cross sections of the tip portion of the insertion tube according to an example 6.

FIGS. 12A-12B illustrate cross sections of a tip portion of an insertion tube according to a reference example 1.

FIGS. 13A-13B illustrate cross sections of the tip portion of the insertion tube according to a reference example 2.

FIGS. 14A-14B illustrate cross sections of the tip portion of the insertion tube according to a reference example 3.

FIG. 15 illustrates a cross section of a tip portion of an insertion tube according to a first variation of the embodiment of the invention.

FIG. 16 illustrates a cross section of a tip portion of an insertion tube according to a second variation of the embodiment of the invention.

DESCRIPTION OF EMBODIMENTS

Figure 2A:
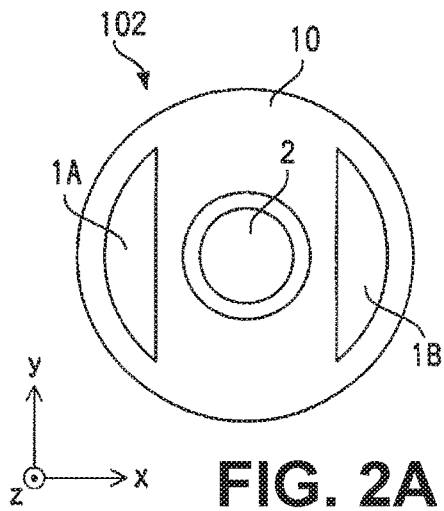
FIGS. 2A-2D illustrate a plan view and a cross sectional view of a tip portion of an insertion tube of the endoscope according to the embodiment of the invention.

Hereinafter, an illumination optical system for an endoscope according to an embodiment of the invention is described with reference to the accompanying drawings.

FIG. 1 illustrates an outer appearance of an endoscope 100 having an illumination optical system 151 according to the embodiment. The endoscope 100 includes a tube-like insertion tube 101 covered with an elastic sheath. At a tip of the insertion tube 101, a tip portion 102 covered with a resin housing having rigidity is provided. A bending part disposed on the front side of the tip portion 102 of the insertion tube 101 is formed to be freely bent through remote operation (specifically, a rotation operation to a bending operation knob 105) from an operation unit 104 coupled to the proximal end of the insertion tube 102. This bending mechanism is a known mechanism installed in a general endoscope, and is configured such that a bending part 103 is bent by drawing of operation wires in conjunction with the rotation operation to the bending operation knob 105. In accordance with change of the direction of the tip portion 102 in response to a bending motion by the above described operations, an imaging area of the endoscope 100 moves.

The illumination optical system 151 is an optical system for illuminating an observation target area and for obtaining an image of the observation target area. As described in detail below, the illumination optical system 151 includes optical components (e.g., a cap 3, convex lenses 8A and 8B) disposed in the tip portion 102, and light guides 4A and 4B provided to extend in the endoscope 100. To obtain an image of the observation target area, object light from the observation target area is converged on a light-receiving surface of an image pickup device 7 in the tip portion 102 (see FIG. 2). The endoscope 100 according to the embodiment is designed, for example, on the assumption of observation for nose and throat. Therefore, the illumination optical system 151 is designed on the assumption that the angle of field of the illumination optical system 151 is approximately 80 degrees to 100 degrees and the diameter thereof is extremely small. A connection part 106 of the endoscope 100 is connected to an external device (not shown). The external device includes a light source, and illumination light for illuminating an observation target area in a wide field of view is supplied to the endoscope 100. Further, the external device receives a signal outputted from the image pickup device of the endoscope 100, executes signal processing and image processing, and then displays an image corresponding to the processed signal on a monitor (not shown).

Figure 2B:
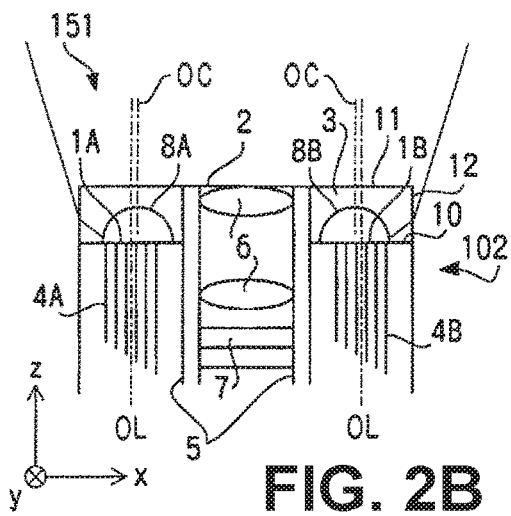

FIGS. 2A and 2B respectively illustrate a plan view and a cross sectional view of the insertion tube 101 of the endoscope 100 according to the embodiment.

On a tip end face 10 of the tip portion 102, two light-distribution windows 1A and 1B and an observation window 2 are provided. Further, on the tip end face 10 of the tip portion 102, a transparent cap 3 is provided to cover the light-distribution windows 1A and 1B. In FIG. 2A, the cap 3 is omitted for the sake of simplicity. The two light-distribution windows 1A and 1B are provided to sandwich the observation window 2 in x-axis direction. The two light-distribution windows 1A and 1B are optically connected to the external device via light guides 4A and 4B, respectively, provided in the inside of the insertion tube 101. The illumination light emitted from the light source of the external device propagates through the light guides 4A and 4B and is emitted from the light-distribution windows 1A and 1B to illuminate the observation target area in a body cavity. The illumination light reflected from the observation target area after emitted from the light-distribution windows 1A and 1B is received as object light through the observation window 2. A cross section of each of the light-distribution windows 1A and 1B in the xy plane is formed such that the length in y-axis direction is longer than the length in x-axis direction, and specifically is formed in a shape of a crescent as shown in FIG. 2A.

The observation window 2 includes an objective lens 6 and an image pickup device 7 held by a cylindrical holding member 5. The image pickup device 7 is connected to the external device via a signal line (not shown) provided in the insertion tube 101. The object light which has been received through the observation window 2 and is converged on the image pickup device 7 is converted into an electric signal by the image pickup device 7, and the electric signal is transmitted to the external device via the signal line. As the image pickup device 7, a CCD (Change Coupled Device) image sensor or a CMOS (Complementary Metal Oxide Semiconductor) image sensor may be used. As the monitor, a laterally long monitor of which aspect ratio of a displaying area is, for example, 4:3 or 16:9 is used.

As shown in FIG. 2B, the observation window 2 is provided at a tip part of the holding member 5 to project toward the tip direction (the positive side in z-axis direction) with respect a surface on which the light-distribution windows 1A and 1B are provided. The holding member 5 is made of material which does not let light pass therethrough so that the illumination light emitted from the light-distribution windows 1A and 1B is prevented from entering the observation windows 2 without illuminating the observation target area. That is, the holding member 5 prevents occurrence of stray light and also prevents deterioration of the image quality.

The cap 3 provided at the tip portion 102 of the insertion tube 101 is formed in a ring-shape to cover the tip end face 10 of the tip portion 102 and not to interfere with the observation window 2. This structure is provided for the purpose of preventing the illumination light entered the cap 3 from being reflected from a boundary of the cap 3 and entering the observation window 2 without illuminating the observation target area (i.e., stray light). As material of the cap 3, resin or glass for letting the illumination light pass therethrough may be used; however, materials of the cap 3 are not limited to these examples.

At positions on the lower surface of the cap 3 (on the negative side in z-axis direction) corresponding to the two light-distribution windows 1A and 1B, concave lens parts 8A and 8B are formed. Each of the concave lens parts 8A and 8B is formed by forming a recessed part on the cap 3 and has a negative refractive power. The cross sectional shape of each of the concave lens parts 8A and 8B of the cap 3 in the xy plane is formed such that the length in y-axis direction is larger than the length in x-axis direction (e.g., a crescent or an elliptical shape). Therefore, each of the concave lens parts 8A and 8B has larger negative power in x-axis direction than the negative power in y-axis direction (i.e., each of the concave lens parts 8A and 8B has a smaller curvature radius of the recession in x-axis direction than that in y-axis direction). The cross section of each of the concave lens parts 8A and 8B in each of the xz plane and the yz plane is a spherical surface, and each of the concave lens parts 8A and 8B functions as an aspherical concave lens of which curvature differ between the cross sections. With this functional aspect, the illumination light which has emitted from the light-distribution windows 1A and 1B after propagating through the light guides 4A and 4B and has propagated through the concave lens parts 8A and 8B is scattered, and the intensity distribution of the scattered light becomes a laterally long distribution which is expanded in x-axis direction.

In this embodiment, the cross sectional shape of each of the concave lens parts 8A and 8B of the cap 3 and the light-distribution windows 1A and 1B is formed in a shape of a crescent in the xy plane so that an area of the tip end face 10 of the tip portion 102 can be used effectively; however, the present invention is not limited to such a configuration. For example, as the cross sectional shape of each of the concave lens parts 8A and 8B in the xy plane, an elliptical shape where the outer diameter in y-axis direction is larger than the outer diameter in x-axis direction or a rectangular shape may be used.

In the embodiment, for the purpose of easing manufacturing, the cross section of each of the concave lens parts 8A and 8b in the xz plane and the yz plane is formed in a spherical shape; however, the present invention is not limited to such a configuration. For example, the cross sectional shape of each of the concave lens parts 8A and 8B in the xz plane and the yz plane may be formed in an aspherical shape, and in this case the same advantageous effects of those of the above described embodiment can be achieved. By employing aspherical surface design, the degree of freedom of light distribution can be enhanced.

The cross section of each of the concave lens parts 8A and 8B according to the embodiment in the xz plane and the yz plane has a spherical shape, and the surface of each of the concave lens parts 8A and 8B is formed to be a toroidal surface of which central symmetric axis is substantially parallel with x-axis; however, the present invention is not limited to such a configuration. For example, the surface of each of the concave lens parts 8A and 8B may be configured to be a toroidal surface of which center symmetric axis is inclined with respect to x-axis in the xz plane. Alternatively, the surface of each of the concave lens parts 8A and 8B may be formed to be an anamorphic surface having different curvatures between x-axis direction and y-axis direction. In these examples, the same advantageous effects as those of the above described embodiment can be achieved.

Optical axes OC of the concave lens parts 8A and 8B of the cap 3 are shifted respectively from optical axes OL of the light-distribution windows 1A and 1B and the light guides 4A and 4B, and the concave lens parts 8A and 8B are disposed to be slightly shifted respectively toward the center of the tip end face 10. As a result, the light distribution windows 1A and 1B are disposed on the outside relative to the concave lens parts 8A and 8B, respectively, and therefore the illumination light which has passed through the concave lens parts 8A and 8B is emitted while being inclined toward the negative side of x-axis and the positive side of x axis, respectively, in comparison with the case where the concave lens parts 8A and 8B are not decentered. As a result, the scattering effect in x-axis direction by the concave lens parts 8A and 8B becomes larger in comparison with the case where the concave lens parts 8A and 8B are not decentered.

The illumination light which has been emitted from the light-distribution windows 1A and 1B and is scattered from the concave lens parts 8A and 8B is emitted from a lateral surface 12 or an upper surface 11 (the positive side in z-axis direction) of the cap 3 after propagating through the cap 3. The intensity distribution of the emitted illumination light becomes a laterally long distribution elongated in x-axis direction. In this embodiment, each of the concave lens parts 8A and 8B of the cap3 has a larger refractive power in x-axis direction, and the concave lens parts 8A and 8B are decentered from the light-distribution windows 1A and 1B, respectively. Therefore, the degree of scattering effect of the illumination light is larger in x-axis direction, and when a monitor having a laterally long displaying area is used, the intensity distribution of the illumination light can be made consistent with the aspect ratio of the monitor. As a result, it becomes possible to prevent decrease of the use efficacy of the illumination light due to the fact that an area not displayed on the monitor is illuminated, and thereby it becomes possible to obtain an image having a high brightness over the entire display area.

Figure 2C:
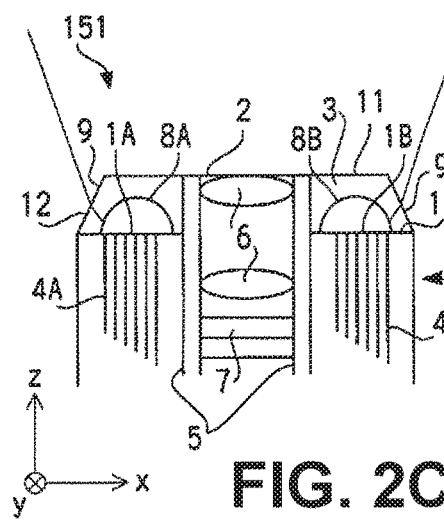
Figure 2D:
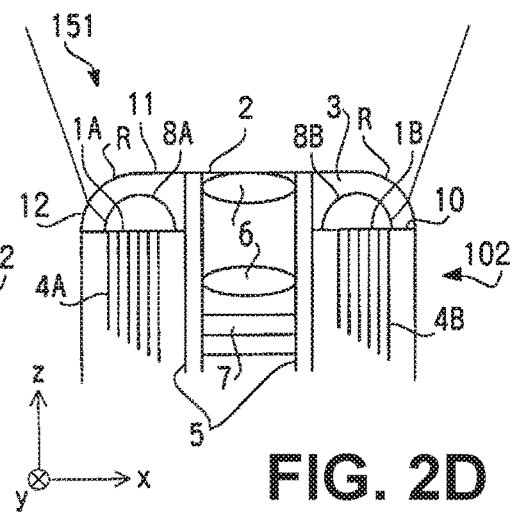

In FIG. 2B, the lateral surface 12 of the cap 3 is formed to be perpendicular to the tip end face 10 of the insertion tube 101; however, as shown in FIG. 2C the lateral surface 12 may be formed to have an inclined surface 9 so that the cap 3 becomes thinner toward the tip side (the positive side in z-axis direction). As a result, it becomes possible to easily insert the insertion tube 101 into a body cavity while decreasing resistance which the cap 3 receives from a body cavity wall. The upper surface 11 and the lateral surface 12 of the cap 3 may not be connected nonconsecutively, but may be connected consecutively via a curved surface R as shown in FIG. 2D. By connecting the lateral surface 12 and the upper surface 11 of the cap 3 via the curved surface R, it becomes possible to decrease resistance received from the body cavity wall when the insertion tube 101 is inserted in the body cavity.

Figure 3:
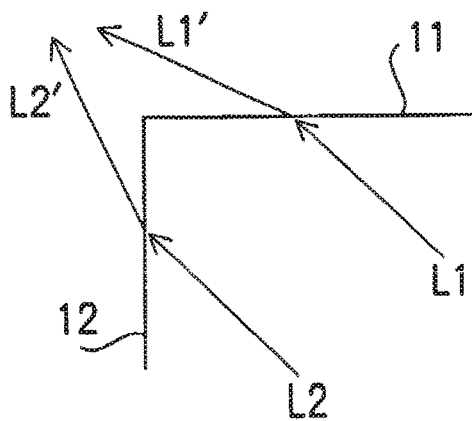
FIG. 3 is a cross section of a cap for explaining light rays of illumination light.

The angle of emission of the illumination light emitted from the lateral surface 12 of the cap 3 becomes smaller than the angle of emission of the illumination light emitted from the upper surface 11 of the cap 3. FIG. 3 illustrates a situation where light rays L1 and L2 of which propagating directions in the cap 3 are in parallel with each other and are refracted by the upper surface 11 and the lateral surface 12, respectively. The light rays L1 and L2 are incident on the upper surface 11 and the lateral surface 12 respectively, and exit therefrom as light rays L1' and L2'. Although each of the light rays L1 and L2 is refracted by the boundary of the cap 3, the light ray L1 is refracted such that the exit angle (the angle between the exit light ray and the axis (the optical axis, z-axis) of the endoscope) of the refracted light ray L1' becomes wider (i.e., the angle between the proceeding direction and the optical axis becomes larger) relative to the proceeding direction of the light ray L1, and the light ray L2 is refracted such that the exit angle of the refracted light ray L2' becomes narrower (i.e., the angle between the proceeding direction and the optical axis becomes smaller) relative to the proceeding direction of the light ray L2. For this reason, in an illumination optical system of a conventional endoscope, it is necessary to decrease the ratio of the illumination light being emitted from the lateral surface 12 of the cap 3, and thereby it becomes necessary to increase the outer diameter of the cap 3. By contrast, according to the embodiment, the scattering effect of the illumination light is large, and thereby it becomes possible to widen the exit angle of the illumination light emitted from the lateral surface 12 of the cap 3. Therefore, it is not necessary to increase the outer diameter of the cap 3, and it is possible to make the tip portion 102 of the insertion tube 101 slender. As a result, it becomes possible to easily insert the insertion tube 101 in a body cavity.

The upper surface 11 and the lateral surface 12 are not provided with special structures like the concave lens parts 8A and 8B formed on the lower surface of the cap 3, but have smooth surfaces. However, the present invention is not limited to such a configuration. For example, in order to suppress Fresnel reflection at the boundary of the upper surface 11 and the lateral surface 12 of the cap 3 and thereby to increase the emission light amount, a diffraction grating or a fine structure may be provided. Material having a high reflectivity (e.g., white coating or a metal mirror) may be provided at the boundary between the cap 3 and the holding member 5 which holds the objective lens 6 or in a portion on the lower surface of the cap 3 other than the areas where the concave lens parts 8A and 8B are formed. With this configuration, it becomes possible to suppress the absorption of the illumination light by the surface of the insertion tube 101 or the holding member 5, and thereby it becomes possible to increase the amount of illumination light emitted to the observation target area.

Since the function of scattering the illumination light and making the intensity distribution laterally long by the concave lens parts 8A and 8B can be realized by forming recessed parts on the lower surface of the cap 3, increase of costs and complication of the configuration of the endoscope 100 can be suppressed.

Hereafter, examples of the illumination optical system 151 for an endoscope according to the embodiment of the invention are described.

As described above, the insertion tube 101 of the endoscope according to the embodiment of the invention includes the light guides 4A and 4B each having the cross sectional shape formed such that the diameter in y-axis direction is longer than the diameter in x-axis direction, and the concave lens parts 8A and 8B having negative powers. By decentering the optical axes OC of the concave lens parts 8A and 8B to the center side of the tip portion 102 in x-axis direction with respect to the optical axes OL of the light guides 4A and 4B, the scattering effect of the emitted light in x-axis direction is increased. Regarding the scattering effect, ray tracing simulation was carried out for the emitted light while changing the material and shape of the cap 3 and the light-distribution windows 1A and 1B (light guides 4A and 4B).

Execution conditions of the simulation are explained with reference to FIG. 4. In the simulation, the widths w of the light-distribution windows 1A and 1B in x-axis direction, the refractive index $n_d$ at d-line of the cap 3, the curvature radius r in x-axis direction of the recessed parts of the concave lens parts 8A and 8B having negative powers, the distance d in x-axis direction from the outer edge in x-axis direction of each of the concave lens parts 8A and 8B to the periphery of the cap 3, the shift amount (decentering amount) s of the optical axes OC of the concave lens parts 8A and 8B with respect to the optical axes OL of the light guides 4A and 4B, and the inclined angle q of the lateral surface 12 of the cap 3 are changed as simulation parameters, and the scattering effect of the concave lens parts 8A and 8B is calculated. When the center O of the tip end face 10 of the tip portion 102 is defined as an origin of a coordinate, the width w represents the width in the x-axis direction passing through the center O. That is, when each of the light-distribution windows 1A and 1B is formed in a crescent shape, the width w becomes the maximum width of the light-distribution windows in x-axis direction. Further, the distance d represents the distance on x-axis. Furthermore, as described above, in order to obtain a wide emission angle, it is desirable to decrease the ratio of the illumination light emitted from the lateral surface 12 of the cap 3. Therefore, it is preferable that the thickness of the cap 3 in z-axis direction is small; however, if the thickness of the cap 3 in z-axis direction is too small, the manufacturing becomes difficult. In this simulation, the thickness of the cap 3 in z-axis direction is defined as 0.5 mm for all the simulation conditions in consideration of easiness of manufacturing. The decentering amount is defined as positive when the optical axes OC of the concave lens parts 8A and 8B are decentered to the center side (inner side) of the tip portion 102 with respect to the optical axes OL of the light guides 4A and 4B. As the exit angle of the illumination light emitted from the light-distribution windows 1A and 1B after propagating through the light guides 4A and 4B, 0 degree and 30 degrees are used for the calculation.

Table 1 shows the calculation conditions for the simulation. In Table 1, the parameters for the calculation conditions and the calculation results of the function f1 and the function f2 indicating the scattering effect of the concave lens parts 8A and 8B are shown. The functions f1 and f2 are expressions for quantifying the scattering effects of the concave lens parts 8A and 8B, and are expressed by the following expressions (1) and (2).

TABLE 1

| | r [mm] | $n_d$ | w [mm] | d [mm] | s [mm] | Function f1 | Function f2 |
|---|---|---|---|---|---|---|---|
| Example 1 | 0.300 | 1.635 | 0.450 | 0.250 | 0.050 | $6.1 \times 10^{-3}$ | $76.6 \times 10^{-06}$ |
| Example 2 | 0.350 | 1.635 | 0.500 | 0.220 | 0.070 | $11.4 \times 10^{-03}$ | $176.3 \times 10^{-06}$ |
| Example 3 | 0.200 | 1.55 | 0.300 | 0.249 | 0.049 | $5.6 \times 10^{-03}$ | $68.1 \times 10^{-06}$ |
| Example 4 | 0.300 | 1.635 | 0.450 | 0.350 | 0.050 | $6.1 \times 10^{-03}$ | $107.3 \times 10^{-06}$ |

TABLE 1-continued

|  | r [mm] | $n_d$ | w [mm] | d [mm] | s [mm] | Function f1 | Function f2 |
|---|---|---|---|---|---|---|---|
| Example 5 | 0.280 | 1.635 | 0.500 | 0.249 | 0.029 | $2.5 \times 10^{-03}$ | $17.7 \times 10^{-06}$ |
| Example 6 | 0.280 | 1.55 | 0.500 | 0.249 | 0.029 | $2.3 \times 10^{-03}$ | $16.8 \times 10^{-06}$ |
| Reference Example 1 | 0.250 | 1.635 | 0.450 | 0.370 | 0.020 | $1.2 \times 10^{-03}$ | $8.7 \times 10^{-06}$ |
| Reference Example 2 | 0.300 | 1.635 | 0.450 | 0.275 | 0.075 | $13.8 \times 10^{-03}$ | $284.5 \times 10^{-06}$ |
| Reference Example 3 | 0.300 | 1.635 | 0.450 | 0.375 | 0.075 | $13.8 \times 10^{-03}$ | $388.0 \times 10^{-06}$ |

$$f1=(n_d \times w \times s^2)/r \quad (1)$$

$$f2=(n_d \times w \times d \times s^3)/r \quad (2)$$

Regarding the function f1, as the refractive index $n_d$ becomes large, the angle of refraction of the illumination light at the boundary of the concave lens parts 8A and 8B becomes large and thereby the scattering effect of the concave lens parts 8A and 8B becomes large. Further, as the decentering amount s becomes large in the positive direction, the degree of inclination toward the outside of the exiting direction of light which has propagated through the concave lens parts 8A and 8B becomes large, and thereby the scattering effect toward the outside becomes large. Further, as the negative power of the concave lens parts 8A and 8B becomes large (i.e., as the curvature radius r of the recessed part becomes small), the scattering effect becomes large. Power of a concave lens becomes larger from the lens center toward the outside. Therefore, as the width w of the light-distribution window becomes large, the ratio of the illumination light passing through the outer portion of the concave lens where power is large becomes large, and thereby the scattering effect becomes large. Thus, the function f1 represents the degree of the scattering effect of the concave lens parts 8A and 8B toward the outside. To highlight the contribution of the decentering to the scattering effect, the decentering amount s is squared and is introduced to the expressions.

The function f2 is provided by adding effect of the outer diameter of the cap 3 to the function f1. The illumination light which is incident on the upper surface 11 of the cap 3 after propagating through the cap 3 is refracted by the upper surface 11 of the cap 3 such that the exit angle is increased. On the other hand, the illumination light which is incident on the lateral surface 12 of the cap 3 is refracted such that the exit angle is decreased. As a result, as the distance d from the outer edge of each of the concave lens parts 8A and B in x-axis direction to the periphery of the cap 3 becomes large, the ratio of the illumination light being emitted from the lateral surface 12 of the cap 3 decreases, and the scattering effect becomes large. When the distance d is small, the ratio of the illumination light being emitted from the lateral surface 12 of the cap 3 increases, and thereby the scattering effect decreases. Therefore, in order to increase the scattering effect, it is necessary to increase the decentering amount. For this reason, the degree of the scattering effect considering the outer diameter of the cap 3 can be represented by the function f2 obtained by multiplying the function f1 by the distance d and the decentering amount s.

The parameters of the examples 1 to 6 are selected so that the functions f1 and f2 satisfy the following conditions (3) and (4).

$$2 \times 10^{-3} < f1 < 13 \times 10^{-3} \quad (3)$$

$$15 \times 10^{-6} < f2 < 200 \times 10^{-6} \quad (4)$$

Each of the conditions (3) and (4) represents a condition for providing the concave lens parts 8A and 8B with the desirable scattering effect as the illumination optical system 151 for an endoscope.

When the function f1 gets larger than or equal to the upper limit of the condition (3), the scattering effect of the concave lens parts 8A and 8B becomes too large and therefore the light which has been emitted from the light-distribution windows 1A and 1B and scattered by the concave lens parts 8A and 8B becomes easy to enter the lateral surface 12 of the cap 3. As described above with reference to FIG. 3, the exit angle of the light emitted from the lateral surface of the cap 3 become smaller than that of the light emitted from the upper surface 11 of the cap 3. Therefore, it is not preferable that the function f1 gets larger than or equal to the upper limit of the condition (3). When the function f1 gents smaller than or equal to the lower limit of the condition (3), the concave lens parts 8A and 8B come short of scattering effect. Since in this case the light emitted from the cap 3 is not sufficiently scattered, it is not desirable that the function f1 gets smaller than or equal to the lower limit. On the other hand, when the function f1 satisfies the condition (3), the scattering effect of the concave lens parts 8A and 8B becomes large, and thereby it becomes possible to suppress the amount of light entering the lateral surface 12 of the cap 3.

The condition (4) has the same significance as that of the condition (3). However, since as described above the function f2 has the effect of the outer diameter of the cap 3, a desirable condition considering the outer diameter of the cap 3 can be obtained from the condition (4). As a result, even when the outer diameter of the cap 3 is changed in accordance with the outer diameter of the insertion tube 101 of the used endoscope 100, a desirable condition for the concave lens parts 8A and 8B can be obtained.

Simulation results are explained for each calculation condition with reference to the drawings. FIG. 5 illustrates an example of the light ray of the illumination light emitted from the light-distribution windows 1A and 1B after propagating through the light guides 4A and 4B. FIG. 5A illustrates the case of the exit angle of the illumination light of 0 degree, and FIG. 5B illustrates the case of the exit angle of the illumination light of 30 degrees. Although the exit angle of the illumination light emitted from the light-distribution windows 1A and 1B varies depending on the thickness of the light guides 4A and 4B and the connection condition between the light source and the light guides 4A and 4B, in general the exit angle of approximately 30 to 40 degrees is used for an endoscope. In the calculation described below, explanations are made by using the simulation results in the case of the exit angles of 0 degree and 30 degrees in consideration of easy understand of the scattering effect according to the embodiment of the invention. The light ray illustrated in regard to the calculation result is a light ray emitted from the outermost position on x-axis in an area of each of the light-distribution windows 11A and 11B. In the following, the explanation is made only for this light ray. This is because as the exit position from the light-distribution windows 11A and 11B gets closer to the outer side, the light becomes easy to enter the lateral surface 12 of the cap 3, the exit angle of the emitted light from the cap 3 tends to become small, and thereby the scattering effect by the concave lens parts 8A and 8B appears directly. In the simulation, the observation window 3, the holding member 5 and the objective lens 6 are not considered for convenience of explanation.

Figures 6A, 6B:
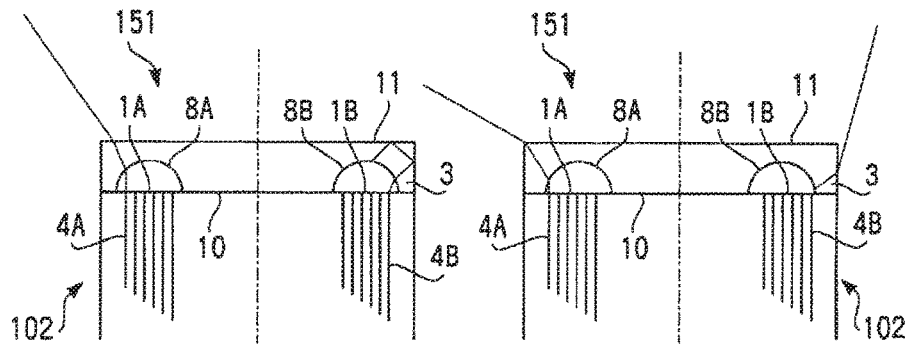
FIGS. 6A-6B illustrate cross sections of the tip portion of the insertion tube according to an example 1.

FIG. 6 illustrates simulation results of the exit light according to the example 1. FIG. 6A illustrates the case of the decentering amount s of zero, and FIG. 6B illustrates the case where the concave lenses 8A and 8B are decentered. The exit angle of the illumination light emitted from the light-distribution window 1A is 0 degree, and the exit angle of the illumination light emitted from the light-distribution window 1B is 30 degrees. When the exit angle is 0 degree, the exit angle of the illumination light is increased by the concave lens parts 8A and 8B regardless of presence/absence of the decentering. However, the exit angle in the case where the concave lens parts 8A and 8B are decentered is larger, and the scattering effect in the case where the concave lens parts 8A and 8B are decentered is larger. In the case of the exit angle of 30 degrees, the exit light from the light-distribution window 1B is totally reflected from the lateral surface 12 and the upper surface 11 of the cap in the inside of the cap 3 and thereby the illumination light cannot be picked up from the cap 3 when the decentering does not exist. On the other hand, when the decentering exists, the illumination light can be picked up from the cap 3 through the lateral surface 12. Thus, by decentering the concave lens parts 8A and 8B to satisfy the conditions (3) and (4), it becomes possible to enhance the scattering effect of the concave lens parts 8A and 8B and thereby it becomes possible to enhance the amount of illumination light.

Figures 7A, 7B:
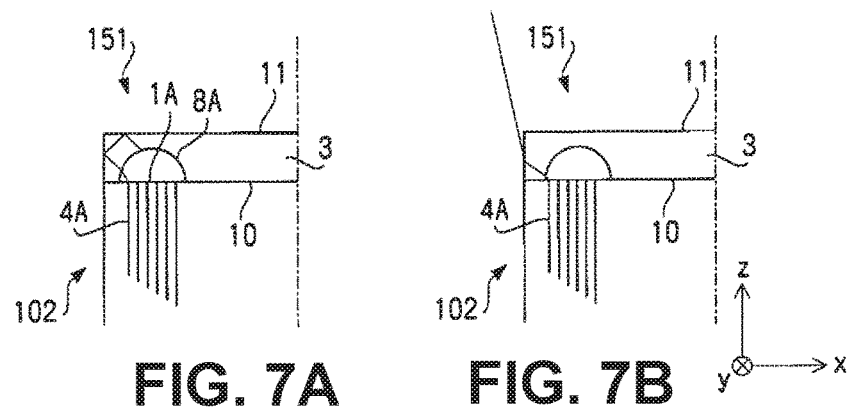
FIGS. 7A-7B illustrate cross sections of the tip portion of the insertion tube according to an example 2.
Figures 8A, 8B:
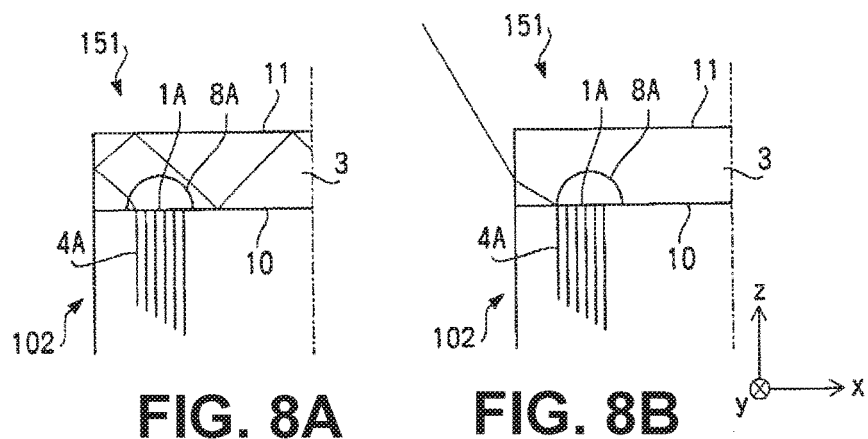
FIGS. 8A-8B illustrate cross sections of the tip portion of the insertion tube according to an example 3.

FIG. 7 illustrates simulation results of emitted light according to the example 2. FIG. 8 illustrates simulation results of emitted light according to the example 3. Each of FIGS. 7A and 8A illustrates the case where, of the parameters of examples 2 and 3, the decentering amount s is set for zero, and each of FIGS. 7B and 8B illustrates the case where, of the parameters of examples 2 and 3, the concave pens part 8A is decentered. The illumination light is emitted at the exit angle of 30 degrees from the light-distribution window 1A. When the decentering does not exist, the light emitted from the light-distribution window 1A is totally reflected by the lateral surface 12 and the upper surface 11 in the cap 3 and therefore is not picked up from the cap 3 to the outside. On the other hand, when the decentering exists, the illumination light having a large exit angle can be picked up from the lateral surface 12 of the cap 3. Thus, according to the examples 2 and 3, by decentering the concave lens parts 8A and 8B, the scattering effect is enhanced and the amount of illumination light is increased.

FIG. 9 illustrates simulation results of emitted light according to the example 4. FIG. 10 illustrates simulation results of emitted light according to the example 5. FIG. 11 illustrates simulation results of emitted light according to the example 6. In the example 4, the inclined surface 9 having the inclination angle of 11.3 degrees is provided as the lateral surface 12 of the cap 3. Each of FIGS. 9A, 10A and 11A illustrates the simulation result when, of the parameters of the examples 4 to 6, the decentering amount s is set for zero. Each of FIGS. 9B, 10B and 11B illustrates the simulation result when the concave lens part 8A is decentered. The illumination light is emitted from the light distribution window 1A at the exit angle of 30 degrees. Regardless of presence/absence of the decentering, the exit angle of the illumination light is increased by the concave lens part 8A, and the exit angle is larger and therefore the scattering effect is larger when the decentering exists in comparison with the case when the decentering does not exist. Thus, according to the examples 4 to 6, by decentering the concave lens parts, the scattering effect is enhanced.

Hereafter, an illumination optical system 451 according to reference examples 1 to 3 shown in Table 1 is explained. In the reference examples 1 to 3, the illumination light which has propagated through a light guide 34 provided in a tip portion 402 of the endoscope is emitted from a light-distribution window 31 (see FIG. 12). The emitted illumination light propagates through a cap 33 and emitted from a lateral surface 42 or an upper surface 41 (the positive side in z-axis direction) of the cap 33. In a portion on the lower surface (the negative side in z-axis direction) of the cap 33 facing the light-distribution window 31, a concave lens part 38 is formed. Parameters user for simulation for the reference examples 1 to 3 are the same as those used for the examples 1 to 6 shown in FIG. 4. The reference examples 1 to 3 do not satisfy the conditions (3) and (4). In the reference example 1, the function f1 is smaller than the lower limit of the condition (3), and the function f2 is smaller than the lower limit of the condition (4). In each of the reference examples 2 and 3, the function f1 is larger than the upper limit of the condition (3), and the function f2 is larger than the upper limit of the condition (4).

FIG. 12 illustrates the simulation result of the emitted light according to the reference example 1. FIG. 12A illustrates the simulation result when, of the parameters of the reference example 1, the decentering amount s is set for zero. FIG. 12B illustrates the simulation result when the concave lens part 38 is decentered. The illumination light is emitted from the light distribution window 31 at the exit angle of 30 degrees. Since the functions f1 and f2 are smaller than the lower limits of the conditions (3) and (4), respectively, the scattering effect is small. By comparing the reference example 1 (FIG. 12) with the example 4 (FIG. 9) where the inclined surface 9 is provided as the lateral surface 12 of the cap 3 and the exit angle of the illumination light is 30 degrees, it is understood that increase of the scattering effect by the decentering in the reference example 1 is smaller than that in the example 4.

FIG. 13 illustrates simulation results of emitted light according to the reference example 2. FIG. 14 illustrates simulation results of emitted light according to reference example 3. Each of FIGS. 13A and 14A illustrates the simulation result when, of the parameters of the reference examples 2 and 3, the decentering amount s is set for zero. Each of FIGS. 13B and 14B illustrates the simulation result when the illumination light is emitted at the exit angle of zero degree. In each of the reference examples 2 and 3, the exit angle is increased when the decentering does not exist. On the other hand, when the decentering exists in each of the reference examples 2 and 3, the functions f1 and f2 are larger than the upper limits of the conditions (3) and (4), respectively. Therefore, the scattering effect is excessive. In the reference example 2, the emitted light is totally reflected by the lateral surface 12 and the upper surface 11 of the cap 33, and therefore cannot be picked up from the cap 33 to the outside. Further, in the reference example 3, the illumination light of which exit angle has increased by the concave lens par 38 is decreased by the lateral surface 12 of the cap 3. Therefore, the scattering effect cannot be obtained.

As described above, in the examples 1 to 6 where the functions f1 and f2 satisfy the conditions (3) and (4), respectively, the concave lens parts 8A and 8B have appropriate scattering effect, and therefore the scattering effect of the illumination light and the intensity of the emitted light are enhanced. On the other hand, in the reference examples 1 to 3 which does not satisfy the conditions (3) and (4), the scattering effect of the concave lens part 38 is excessive or short, and therefore the amount of light emitted from the lateral surface of the cap 33 increases and the emitted light becomes hard to be scattered or the emitted light is totally reflected by the lateral surface of the upper surface in the cap 33 and therefore the effect of picking up the illumination light to the outside of the cap 33 decreases.

Hereafter, an illumination optical system according to a first variation of the embodiment of the invention is described.

FIG. 15 is a cross sectional view of a tip portion 202 of an endoscope having an illumination optical system 251 according to the first variation. The tip portion 202 of the endoscope shown in FIG. 15 has the same configuration as that of the tip portion 102 of the endoscope 100 shown in FIG. 2 excepting that disposition of the light-distribution windows in the tip portion 202 is different from that of the tip 102 and the shape of the lower surface of a cap 3A is changed in conformity with the disposition of the light-distribution windows. The illumination optical system 251 includes optical components (the cap 3A, concave lens parts 8A and 8B, and etc.) disposed in the tip portion 202, and the light guides 4A and 4B provided to extend in the endoscope 100.

In the embodiment shown in FIG. 2, the light-distribution windows 1A and 1B are disposed to be parallel with the upper surface 11 of the cap 3, and the optical axes OL of the light guides 4A and 4B are perpendicular to the light distribution windows 1A and 1B. By contrast, the light-distribution windows 1C and 1D according to the first variation are disposed to be inclined such that the light-distribution windows 1C and 1D become lower at a point closer to the observation window 2 from the periphery of the tip portion 202 in x-axis direction. Further, the surface of each of the light-distribution windows 1C and 1D is not perpendicular to the optical axes OL of the light guides 4A and 4B. Further, the lower surface of the cap 3A is formed to be inclined to be consistent with the light-distribution windows 1C and 1D disposed obliquely. Further, the concave lens parts 8A and 8B are formed on the obliquely formed lower surface of the cap 3 at positions corresponding to the light-distribution windows 1C and 1D. There is no necessity to decenter the optical axes OC of the concave les parts 8A and 8B with respect to the optical axes OL of the light guides 4A and 4B.

As described above, by disposing the light-distribution windows 1C and 1D to be inclined with respect to the optical axes of the light guides 4A and 4B, the illumination light which has propagated through the light guides 4A and 4B is emitted while being broadened outward in x-axis direction by the refraction at the light-distribution windows 1C and 1D in comparison with the case where the light-distribution windows are disposed in the longitudinal direction. Accordingly, the scattering effect can be enhanced.

The optical exes of the concave lens parts 8A and 8B may be decentered toward the center of the tip portion 202 with respect to the optical axes of the light guides 4A and 4B. As a result, the illumination light which has passed through the concave lens parts 8A and 8B can be emitted to be broadened outward in x-axis direction. Therefore, the scattering effect can be enhanced further in comparison with the case where the decentering does not exist.

The optical axes of the concave lens parts 8A and 8B may be decentered to the center of the tip portion 202 with respect to the optical axes of the light guides 4A and 4B. In this case, it is possible to let the illumination light which has passed through the concave lens parts 8A and 8B be widened toward the outside in x-axis direction. Therefore, the scattering effect can be enhanced in comparison with the case where the decentering does not exist.

Hereafter, a second variation of an illumination optical system for an endoscope is described.

FIG. 16 is a cross sectional view of a tip portion 302 of an endoscope having an illumination optical system 351 according to the second variation of the embodiment. The tip portion 302 of the endoscope shown in FIG. 16 has the same configuration as that of the tip portion 102 of the endoscope 100 shown in FIG. 2 excepting that disposition of light-distribution window 1E and 1F in the tip portion 302 is different from that of the tip portion 102, the shape of the lower surface of a cap 3B is changed in conformity with the disposition of the light-distribution windows 1E and 1F, and the disposition of the light guides 4A and 4B in the tip portion 302 is different from that in the tip portion 102. The illumination optical system 351 includes optical components (the cap 3B, concave lens parts 8A and 8B, and etc.) disposed in the tip portion 302, and the light guides 4A and 4B provided to extend in the endoscope 100.

In the embodiment shown in FIG. 2, the optical axes OL of the light guides 4A and 4B are parallel with the axis direction (z-axis direction) of the tip portion 102 and the insertion tube 101 of the endoscope 100. By contrast, in the second variation shown in FIG. 16, the light guides 4A and 4B are parallel with the insertion tube 101, but are disposed to spread out toward the tip side (to the positive side in z-axis direction) in the region of the tip portion 302 of the insertion tube 101. The light-distribution windows 1E and 1F are disposed to be perpendicular to the optical axes of the light guides 4A and 4B in the tip portion 302. That is, the light-distribution windows 1E and 1F are obliquely disposed so that the light-distribution windows 1E and 1F becomes higher at a point closer to the observation window 2 with respect to the outer periphery of the tip portion 302 in x-axis direction. Further, the lower surface of the cap 3B is also inclined to be consistent with the inclined light-distribution windows 1E and 1F. The concave lens parts 8A and 8B are formed on the obliquely formed lower surface of the cap 3B at positions corresponding to the light-distribution windows 1E and 1F. In the tip portion 302, the optical axes of the light guides 4A and 4B are not parallel with the z-axis, but are inclined toward the positive and negative sides in x-axis direction to deviate from the center of the tip portion 302 toward the positive side in z-axis direction.

As described above, since the light guides 4A and 4B are disposed such that the optical axes thereof spread out outward, the illumination light which has propagated through the light guides 4A and 4B are emitted from the light-distribution windows to spread out outward in x-axis direction in comparison with the case where in the tip portion the light guides 4A and 4B are disposed to be parallel with the axis direction (z-axis direction) of the tip portion 302. As a result, the scattering effect can be enhanced.

Further, when the optical axes of the concave lens parts 8A and 8B are defined to be parallel with the optical axes of the light guides 4A and 4B, the optical axes of the concave lens parts 8A and 8B may be decentered toward the center of the tip portion 302 with respect to the optical axes of the light guides 4A and 4B in the tip portion 302. As a result, it becomes possible to let the illumination light which has propagated through the concave lens parts 8A and 8B exit while spreading out in x-axis direction. Consequently, the scattering effect can be further enhanced.

The foregoing is explanation about the embodiment of the present invention; however, the present invention is not limited to the above described embodiment, but can be varied within the scope of the invention.

The invention claimed is:

1. An illumination optical system for an endoscope provided in an elastic insertion tube of an endoscope, comprising:
   two light guides disposed in the insertion tube and arranged in a first direction to sandwich a center of the insertion tube therebetween;
   an observation window disposed on a tip end face of a tip portion of the insertion tube;
   a cap having a circular outer shape and comprising a transparent material for letting the illumination light to pass therethrough, the cap being provided on a front of the end faces of the two light guides,
   two concave lens parts having negative powers, the two concave lens parts being disposed to sandwich the observation window at positions facing the end faces of the two light guides on the tip end face of the insertion tube,
   wherein:
   on the tip end face of the tip portion of the insertion tube, the end face of each of the two light guides has a smaller width in the first direction than a width thereof in a second direction perpendicular to the first direction;
   each of the two concave lens parts comprise a recessed part on a surface of the cap facing the end faces of the two light guides;
   each of the two concave lens parts has a larger negative power in the first direction than a negative power thereof in the second direction; and
   optical axes of the two concave lens parts are decentered from optical axes of the two light guides, respectively;
   wherein when w (unit: mm) represents a width of each of the end faces of the two light guides in the first direction, r (unit: mm) represents a radius of curvature of each of the two concave lens parts in the first direction, s (unit: mm) represents a decentering amount of the optical axis of each of the two concave lens parts toward a center of the insertion tube with respect to the optical axis of a corresponding one of the two light guides, and $n_d$ represents a refractive index at d-line of material of the cap, the illumination optical system satisfies a relationship:

$$2 \times 10^{-3} < (n_d \times w \times s^2)/r < 13 \times 10^{-3}$$

of illumination light which has propagated through each of the two concave lens parts after being emitted from each of the two light guides, an optical path of light which has propagated through a center of each of the two light guides and has been emitted from a center of each end face of each of the two light guides is inclined outward in the first direction with respect to an axis direction of the insertion tube.

2. The illumination optical system for an endo scope according to claim 1, wherein when d (unit: mm) represents a distance, in the first direction passing through a center of the tip end face of the insertion tube, between an outer edge of the cap, the illumination optical system further satisfies a relationship:

$$15 \times 10^{-6} < (n_d \times w \times d \times s^3)/r < 200 \times 10^{-6}.$$

3. The illumination optical system for an endo scope according to claim 1,
   wherein the cap is configured such that an outer diameter of the cap becomes smaller toward a tip of the insertion tube.

* * * * *